United States Patent [19]

Orban

[11] Patent Number: 4,507,463

[45] Date of Patent: Mar. 26, 1985

[54] PROCESS FOR PRODUCING POLYESTERS FROM ALIPHATIC DICARBOXYLIC ACIDS AND POLYALKYLPIPERIDYLDIOLS

[75] Inventor: Ivan Orban, Basel, Switzerland

[73] Assignee: Ciba-Geigy Corporation, Ardsley, N.Y.

[21] Appl. No.: 606,077

[22] Filed: May 1, 1984

[30] Foreign Application Priority Data

May 11, 1983 [CH] Switzerland ........................ 2591/83

Jun. 27, 1983 [CH] Switzerland ........................ 3495/83

[51] Int. Cl.[3] .............................................. C08G 63/34

[52] U.S. Cl. .................................... 528/279; 528/283; 528/291; 528/485; 528/501

[58] Field of Search ............... 528/279, 283, 289, 291, 528/485, 501

[56] References Cited

U.S. PATENT DOCUMENTS

| | | | |
|---|---|---|---|
| 3,444,139 | 5/1969 | Jeurissen et al. | 528/279 |
| 4,222,931 | 9/1980 | Minagawa et al. | 528/291 X |
| 4,233,412 | 11/1980 | Rody et al. | 525/167 |
| 4,234,707 | 11/1980 | Rody et al. | 528/291 X |

*Primary Examiner*—Lucille M. Phynes

*Attorney, Agent, or Firm*—Luther A. R. Hall

[57] ABSTRACT

A novel process for producing compounds of the formula I $$H\left[O-\underset{\text{2,2,6,6-tetramethylpiperidin-4,1-diyl}}{\overset{(CH_3)_2\quad (CH_3)_2}{\bigcirc}}N-R_1-O\overset{O}{\overset{\|}{C}}-R_2-\overset{O}{\overset{\|}{C}}O\right]_n OR_3 \qquad (I)$$

by polycondensation of a diol of the formula II $$HO-\underset{\text{2,2,6,6-tetramethylpiperidin-4,1-diyl}}{\overset{(CH_3)_2\quad (CH_3)_2}{\bigcirc}}N-R_1-OH \qquad (II)$$

with a dicarboxylic acid ester of the formula III $$R_3O-\underset{\|}{\overset{}{C}}-R_2-\underset{\|}{C}-OR_3. \qquad (III)$$
$$\quad\;\; O \qquad\;\; O$$

$R_1$ and $R_2$ are independently alkylene or alkenylene, $R_3$ is lower alkyl and n is 18 to 25.

The process according to the invention is characterized in that the reaction medium is treated, in the presence of at least 0.05 mol %, relative to the diol of the formula II, of an organometallic compound of titanium or tin, at a maximum steam temperature of 75° C., until the formed methanol has been almost completely distilled off; distillation is then continued for at least 3 hours, during which time the volume of the reaction solution is kept approximately constant by successive additions of solvent, at a steam temperature of between 100° and 145° C.; the reaction solution is subsequently concentrated by evaporation, and the melt which remains is finally ground after it has solidified.

There are thus surprisingly obtained, in practically quantitative yield, polyesters of the formula I having a mean molecular weight $\overline{M}n$ of at least 5000.

6 Claims, No Drawings

PROCESS FOR PRODUCING POLYESTERS FROM ALIPHATIC DICARBOXYLIC ACIDS AND POLYALKYLPIPERIDYLDIOLS

The present invention relates to a novel process for producing polyesters from aliphatic dicarboxylic acids and polyalkylpiperidyldiols by reaction of a corresponding diol with an aliphatic dicarboxylic acid under distilling conditions but with a constant volume of reaction solution in the presence of catalytic amounts of a suitable catalyst.

The production of a polysuccinate of 1-(2-hydroxyethyl)-2,2,6,6-tetramethyl-4-hydroxypiperidine is already known from the German Offenlegungsschrift No. 2,719,131 (Example 1). According to the method described therein, the reaction is performed in xylene in the presence of at least 7 mol % of catalyst, relative to the piperidine compound, at 100°–145° C., with removal by distillation of the formed methanol. There is formed in the process, with a final concentration of the product in the reaction solution of about 65% by weight, a polysuccinate having a mean molecular weight $\overline{M}n$ of maximum 4000. The yellowish product obtained does not however fully satisfy, with regard to colour, the present-day requirements in technology.

It has now been found that by carrying out the reaction, likewise under distilling conditions, but with a volume of reaction solution maintained constant by successive additions of solvent, and with the use of suitable catalysts in considerably smaller amounts, there are surprisingly obtained, in practically quantitative yield, polyesters of the aforementioned type having a higher mean molecular weight $\overline{M}n$ of at least 5000, which are perfectly satisfactory with respect to colour. Such polyesters, which are in general known to be valuable stabilisers for organic materials, are particularly suitable, by virtue of their higher $\overline{M}n$ value, for specific applications.

The present invention accordingly relates to a process for producing compounds of the formula I

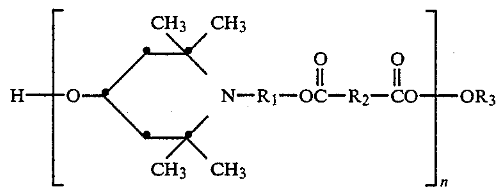

wherein n is a number between 18 and 25, preferably between 19 and 22, $R_1$ and $R_2$ independently of one another are $C_1$–$C_{18}$-alkylene, $C_2$–$C_{18}$-alkylene interrupted by —O—, —S— or —N(R)—, where R is hydrogen or $C_1$–$C_4$-alkyl, or are $C_4$–$C_8$-alkenylene, and $R_3$ is $C_1$–$C_4$-alkyl, by polycondensation of a diol of the formula II

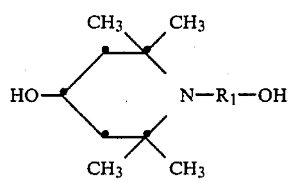

with a dicarboxylic acid ester of the formula III

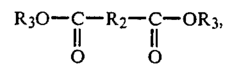

in the molar ratio of about 1:1, in a suitable solvent, which process comprises treating the reaction medium, in the presence of at least 0.05 mol %, relative to the diol of the formula II, of an organometallic compound of titanium or tin, at a maximum steam temperature of 75° C., preferably 69° to 71° C., until the formed methanol has been almost completely distilled off; then continuing distillation for at least 3 hours, preferably 3½ to 5 hours, during which time the volume of the reaction solution is kept approximately constant by successive additions of solvent, at a steam temperature of between 100° and 145° C., preferably between 135° and 140° C.; and subsequently concentrating the reaction solution by evaporation; and finally grinding the resulting melt after solidification.

Suitable catalysts are for example those of the formulae IV and V $$(R_4O)_4\text{—Ti} \qquad (IV)$$

$$\begin{matrix} R_5 \\ & \diagdown \\ & & Sn{=}O \\ & \diagup \\ R_5 \end{matrix} \qquad (V)$$

wherein $R_4$ is $C_1$–$C_{18}$-alkyl, phenyl or benzyl, and $R_5$ is $C_4$–$C_{18}$-alkyl.

Dibutyltin oxide and especially tetrabutyl-o-titanate are preferred.

As $C_1$–$C_{18}$-alkylene, $R_1$ and $R_2$ are preferably $C_2$–$C_6$-alkylene, for example methylene, dimethylene, trimethylene, tetramethylene, hexamethylene, 2,2-dimethyltrimethylene, octamethylene, nonamethylene, decamethylene, dodecamethylene or octadecamethylene. Ethylene is preferred.

As $C_2$–$C_{18}$-alkylene interrupted by —O—, —S— or —N(R)—, $R_1$ and $R_2$ are for example: 2-thiapropylene-1,3, 3-thiapentylene-1,5, 4-oxaheptamethylene-1,7, 3,6-dioxaoctamethylene-1,8 or 3,6-diazaoctamethylene-1,8.

If any substituents are $C_1$–$C_4$-alkyl, they are: methyl, ethyl, n-propyl, isopropyl, n-butyl, sec-butyl or tert-butyl. As $C_1$–$C_{18}$-alkyl, $R_4$ is additionally for example: n-pentyl, 2,2-dimethylpropyl, n-hexyl, 2,3-dimethylbutyl, n-octyl, 1,1,3,3-tetramethylbutyl, nonyl, decyl, dodecyl, hexadecyl or octadecyl. As $C_4$–$C_{18}$-alkyl, $R_5$ is for example: n-butyl, sec-butyl, tert-butyl, n-pentyl, n-hexyl, n-octyl, 1,1,3,3-tetramethylbutyl, n-decyl, n-dodecyl, n-hexadecyl or n-octadecyl. $R_4$ and $R_5$ are preferably n-butyl.

When $R_1$ and $R_2$ are $C_4$–$R_8$-alkenylene, they are for example 2-butenylene-1,4.

The catalysts are used in amounts of at least 0.05 mol %, preferably however between 0.1 and 1.0 mol %, relative to the diol of the formula II.

Suitable solvents are inert, especially aromatic solvents, for example toluene or xylene. Xylene is preferred. The solvent is placed into the reaction vessel in an amount of 100 to 200% by weight, relative to the diol of the formula II, and it must be ensured when successive additions are made that the volume of the reaction solution remains approximately constant, that is to say, with a variation not exceeding 30 vol %, preferably 15 vol %, and in particular 10 vol %.

After completion of the reaction, it is advantageous to filter the reaction solution in order to remove any insoluble constituents present and the catalyst. With the use of a catalyst soluble in the solvent, for example tetrabutyl-o-titanate, the procedure is as follows: the reaction solution is cooled preferably to 80° to 100° C.; there are then added 1 to 3% by weight of a customary filtering auxiliary (for example ®Celite 545) and 10 to 15% by weight of water, relative to the diol of the formula II, and the reaction solution is refluxed for a short time and subsequently azeotropically freed from water. Filtration is preferably performed at 120°-130° C.

By virtue of the process according to the present invention, there is also ensured a clearly better space-time yield.

The process of the invention is of particular interest for producing compounds of the formula VI

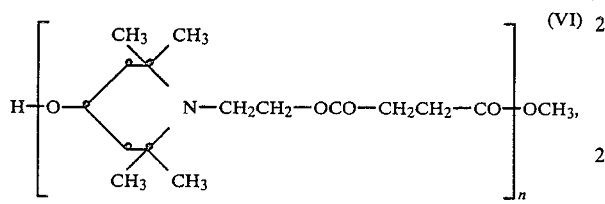

wherein n is a number between 18 and 25, by polycondensation of 1-(2-hydroxyethyl)-2,2,6,6-tetramethyl-4-hydroxypiperidine with dimethyl succinate in the molar ratio of about 1:1 in a suitable solvent, which process comprises treating the reaction medium in the presence of tetrabutyl-o-titanate, at a maximum steam temperature of 75° C., until the formed methanol has been almost completely distilled off; and afterwards continuing distillation for at least 3 hours, during which time the volume of the reaction solution is maintained approximately constant by successive additions of solvent, at a steam temperature of between 100° and 145° C.; subsequently concentrating the reaction solution by evaporation; and finally grinding the resulting melt after solidification.

The compounds of the formula I are valuable stabilisers for organic materials which are subject to decomposition, preferably for synthetic polymers.

The following Examples further illustrate the present invention without limiting the scope thereof.

EXAMPLE 1

171.1 g of 1-(2-hydroxyethyl)-2,2,6,6-tetramethyl-4-hydroxypiperidine and 225 g of xylene are placed into a 750 ml flask with a distilling column. The mixture is heated and water is azeotropically removed; the mixture is then cooled to 130° C., and there are successively added 124.4 g of dimethyl succinate and 0.8 g (0.28 mol %, relative to the hydroxypiperidine derivative) of tetrabutyl-orthotitanate. The formed methanol is distilled off at a steam temperature controlled at a maximum of 70° C., and after 1½ hours this distillation step is practically finished. The mixture is subsequently further distilled for 3½ hours at a steam temperature of about 137° C., the rate of distillation being adjusted to about 100 ml/h. The volume in the flask is kept constant by successive additions of all together about 350 ml of xylene. The solution is cooled to 90° C., and 20 ml of water and 3 g of filtering auxiliary Celite 545 are added. The mixture is refluxed for 15 minutes, and then azeotropically freed from water. The suspension is clarified at 120°-130° C. through a vacuum filter, and the clear filtrate is concentrated by evaporation; the melt remaining behind is cooled and, after solidifying, is finally ground. The yield is 240 g (99.8% of theory) of polysuccinate in the form of colourless to faintly yellowish powder; $\overline{M}n$ value: 5500-6000; softening point from 70° C.

EXAMPLE 2

Reaction and further processing are carried out in a manner analogous to that of Example 1, except that distilling is performed for 5 hours at the steam temperature of about 137° C., during which time the volume of the reaction solution is kept constant. The result is the same as in Example 1, the $\overline{M}n$ value being however 6500-7000.

EXAMPLE 3

The process is repeated exactly as in Example 1 with the exception that only 0.2 g of tetrabutyl-orthotitanate (0.07 mol %, relative to the hydroxypiperidine derivative) is used in place of 0.8 g, and that distillation is performed for 10 hours at a steam temperature of 137° C. instead of for 3½ hours. There is obtained, in practically quantitative yield, a product having an $\overline{M}n$ value of 10,500-11,000; softening point from 106° C.

EXAMPLE 4

The process is repeated exactly as in Example 1 except that, in place of 0.8 g of tetrabutyl-orthotitanate, 1.0 g of dibutyltin oxide (0.5 mol %, relative to the hydroxypiperidine derivative) is used, and that the reaction solution is further distilled for 5 hours at a steam temperature of 137° C. instead of for 3½ hours. There is thus obtained, in practically quantitative yield, a product having an $\overline{M}n$ value of 13,000-13,500; softening point from 120° C.

EXAMPLE 5

The procedure is carried out exactly as in Example 1 except that, in place of 0.8 g of tetrabutylorthotitanate, 0.1 g of dibutyltin oxide (0.05 mol %, relative to the hydroxypiperidine derivative) is used, and that further distilling is performed for 10 hours at a steam temperature of 145° C. instead of for 3½ hours at 137° C. There is obtained, in practically quantitative yield, a product having an $\overline{M}n$ value of 5500-6000; softening point from 70° C.

What is claimed is:

1. A process for producing a compound of the formula I

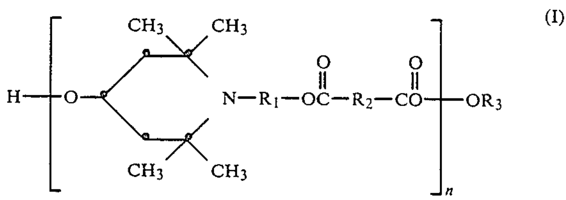

wherein n is a number between 18 and 25, $R_1$ and $R_2$ independently of one another are $C_1$-$C_{18}$-alkylene, $C_2$-$C_{18}$-alkylene interrupted by —O—, —S— or —N(-R)—, where R is hydrogen or $C_1$-$C_4$-alkyl, or are $C_4$-$C_8$-alkenylene, and $R_3$ is $C_1$-$C_4$-alkyl, by polycondensation of a diol of the formula II

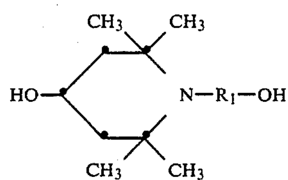

with a dicarboxylic acid ester of the formula III

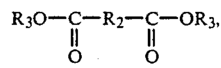

in the molar ratio of about 1:1, in a suitable solvent, which process comprises treating the reaction medium, in the presence of at least 0.05 mol %, relative to the diol of the formula II, of an organometallic compound of titanium or tin, at a maximum steam temperature of 75° C., until the formed methanol has been almost completely distilled off; then continuing distillation for at least 3 hours, during which time the volume of the reaction solution is kept approximately constant by successive additions of solvent, at a steam temperature of between 100° and 145° C.; subsequently concentrating the reaction solution by evaporation; and finally grinding the resulting melt after solidification.

2. A process according to claim 1 for producing a compound of the formula VI

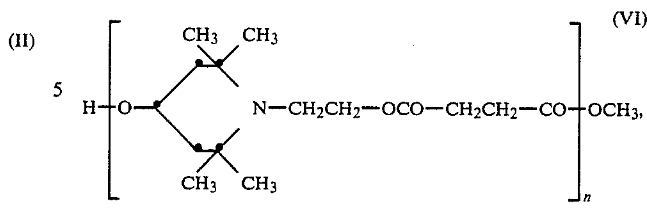

wherein n is a number between 18 and 25, by polycondensation of 1-(2-hydroxyethyl)-2,2,6,6-tetramethyl-4-hydroxypiperidine with dimethyl succinate in the molar ratio of about 1:1 in a suitable solvent, which process comprises treating the reaction medium in the presence of tetrabutyl-o-titanate, at a maximum steam temperature of 75° C., until the formed methanol has been almost completely distilled off; and afterwards continuing distillation for at least 3 hours, during which time the volume of the reaction solution is maintained approximately constant by successive additions of solvent, at a steam temperature of between 100° and 145° C.; subsequently concentrating the reaction solution by evaporation; and finally grinding the resulting melt after solidification.

3. A process according to claim 1, wherein the solvent is xylene.

4. A process according to claim 1, wherein the catalyst is tetrabutyl-o-titanate.

5. A process according to claim 1, wherein the treatment is performed until the formed methanol has been almost completely distilled off at a steam temperature of 69° to 71° C.

6. A process according to claim 3, wherein the distillation is continued, after the formed methanol has been distilled off, for 3½ to 5 hours, with successive additions of xylene, at a steam temperature of between 135° and 140° C.

* * * * *